United States Patent [19]

Schroeder

[11] Patent Number: 5,758,656
[45] Date of Patent: Jun. 2, 1998

[54] STYLET FOR CONTROLLED DEFORMATION OF A TUBE

[76] Inventor: Michael Schroeder, 77 Senson, White Cloud, Mich. 49349

[21] Appl. No.: 712,083

[22] Filed: Sep. 11, 1996

Related U.S. Application Data

[60] Provisional application No. 60/003,680, Sep. 11, 1995.
[51] Int. Cl.$^6$ ........................................... A61B 5/00
[52] U.S. Cl. ........................ 128/772; 604/95; 604/280
[58] Field of Search .................... 604/164, 95, 280; 128/656, 657, 658, 772

[56] References Cited

U.S. PATENT DOCUMENTS

| | | | |
|---|---|---|---|
| 2,574,840 | 11/1951 | Pieri et al. | 128/349 |
| 4,180,076 | 12/1979 | Betancourt | 128/349 |
| 5,123,421 | 6/1992 | Sinofsky | |
| 5,195,968 | 3/1993 | Lundquist et al. | 604/95 |
| 5,259,377 | 11/1993 | Schroeder | 128/207.14 |
| 5,336,182 | 8/1994 | Lundquist et al. | 604/95 |
| 5,358,478 | 10/1994 | Thompson et al. | 604/95 |
| 5,363,861 | 11/1994 | Edwards | 128/772 |

*Primary Examiner*—Sam Rimell
*Assistant Examiner*—Luke Yeh
*Attorney, Agent, or Firm*—Foley & Lardner

[57] ABSTRACT

A tube and stylet assembly for the controlled deflection of the tube is shown. The stylet is received in the lumen of the tube. The stylet includes a first filament having proximal and distal ends and a second filament having proximal and distal ends wherein the proximal and distal ends of the second filament are joined to the first filament such that a surface of the second filament abuts a surface of the first filament. Deflection of the first and second filaments along a plane substantially perpendicular to the abutting surfaces of the first and second filaments necessarily results in a corresponding, opposite deflection of the first and second filaments a spaced distance from the first deflection point. Therefore, a user can control deflection of one portion of the tube and stylet through manipulation of a second portion of the tube and stylet. This structure is particularly useful in inserting a gastric tube either nasally or orally.

19 Claims, 7 Drawing Sheets

STYLET FOR CONTROLLED DEFORMATION OF A TUBE

This application claims the benefit of U.S. Provisional application Ser. No. 60/003,680 filed on Sep. 11, 1995.

BACKGROUND OF THE INVENTION

1. Field of the Invention

This invention relates to a hollow tube and, more particularly, to a stylet which can be manipulated to deflect the tube in which the stylet is received. In another aspect, this invention relates to a method for inserting a tube into a patient's stomach through the nose or mouth.

2. Description of the Related Art

Hollow tubes have numerous applications in the medical field. For example, hollow tubes can be inserted through a patient's nose or mouth and be received in the stomach for either removing fluid and material therefrom or providing food or nutrients to a patient. In another application of tube and stylet assemblies, a tube can be inserted into a patient's nose or mouth and received into the tracheal opening for providing oxygen to a patient's lungs. Numerous other applications of tubes exist.

One significant problem in properly inserting a tube into a patient for the applications described above is controlling the tube during the insertion process. The nasal and oral passageways have significant contours making it difficult to properly insert the tube without causing undue trauma to the tissue of the passageway. Attempts at controlling this deformation of the tube are seen in U.S. Pat. No. 5,259,377 to Schroeder; U.S. Pat. No. 4,180,076 to Betancourt; U.S. Pat. Nos. 5,195,968 and 5,336,182 to Lundquist et al.; U.S. Pat. No. 5,358,478 to Thompson et al.; and U.S. Pat. No. 2,574,840 to Pieri et al. The prior art attempts have failed to create a stylet which can be controlled in multiple directions and which is simple and easy to manufacture and operate.

SUMMARY OF THE INVENTION

A stylet and tube assembly particularly useful for inserting a gastric tube either nasally or orally is shown. The stylet and tube assembly comprises a tube having a proximal end, a distal end and a body intermediate the proximal and distal ends. A lumen extends through the tube and a stylet is telescopically received therein. The stylet comprises a first filament having a proximal end, a distal end and a body portion intermediate the proximal and distal ends. The stylet also includes a second filament having a proximal end, a distal end and a body portion intermediate the proximal and distal ends. The ends of the second filament are joined to the first filament such that the longitudinal axes of the first and second filaments define a plane. With this structure, deflection of the stylet in a first direction, substantially along the plane results in a corresponding, opposite second deflection of the stylet along the plane. With this structure, a user can manipulate a tube and stylet to match the convoluted contour of a passageway in which the tube and stylet are being inserted, such as the nasal or oral passageway to the stomach.

In a preferred embodiment, the first and second filaments each have a substantially flat surface extending longitudinally along a portion of the length thereof. The filaments are joined to one another such that the first and second filaments abut one another. The flat surfaces are adapted to slide along one another as the stylet is deflected along the plane of curvature.

Preferably, the first and second filaments are D-shaped in cross section and the second filament is joined to the first filament by a process such as heat staking, welding, or adhesive. Alternatively, the stylet can be injection molded or extruded and then slit along a portion of the length thereof to create the first and second filaments therefrom. Other suitable cross sectional shapes include rectangular, square, triangular, oval, circular and slotted.

In another aspect, the invention comprises a method for nasally or orally inserting a tube into a patient's stomach. The method begins by providing a tube and stylet as described above. The distal end of the tube and stylet are inserted into either the patient's nose or mouth. Next, a portion of the stylet which remains outside of the patient's nose or mouth is deflected to create a radius of curvature which lies substantially along the plane of curvature. This necessarily results in a corresponding, opposite deflection of the stylet and tube which are received inside the patient's nasal or oral passageway. The portion of the tube and stylet outside of the patient are deflected according to the anatomical curvature of the patient's oral or nasal passageway thereby permitting easier insertion. The tube is ultimately received in the patient's stomach and the stylet is removed therefrom such that the tube may be used for removing fluid and material therefrom or providing fluid thereto.

BRIEF DESCRIPTION OF THE DRAWINGS

The invention will now be described with reference to the drawings in which.

DETAILED DESCRIPTION OF THE PREFERRED EMBODIMENTS

Referring now to the drawings and to FIGS. 1–5 in detail, a tube and stylet assembly 12 according to the invention is shown. The assembly 12 comprises a pliable tube 14 having a deformable stylet 16 telescopically received therein. The tube 14 comprises a proximal end 20, a distal end 22 and a body 24 intermediate the proximal and distal ends. A conventional luer fitting 26 is provided on the proximal end 20 and is mounted to suitable machinery such as a suction apparatus or a fluid injection apparatus (not shown) depending upon the application of tube 14. A primary lumen 28 extends from the proximal end 20 to the distal end 22 of the tube 14. The preferred embodiment of the tube 14 further comprises a secondary lumen 30 which similarly extends from the proximal end 20 to the distal end 22. The secondary lumen 30 is integrally formed in the tube 14 such that the proximal end of the lumen 30 terminates at a fluid conduit 32 extending outwardly from the tube 14 through a suitable aperture. The fluid conduit 32 has a conventional fitting (not shown) mounted thereon for connecting the secondary lumen 30 to a source of suction, pressurized fluid or other apparatus, depending upon the application of the tube 14. The secondary lumen 30 is often included in conventional gastric tubes. However, this element is by no means a requirement of the invention and a tube having a single lumen certainly falls within the scope of the invention.

Figures 1, 2, 3:
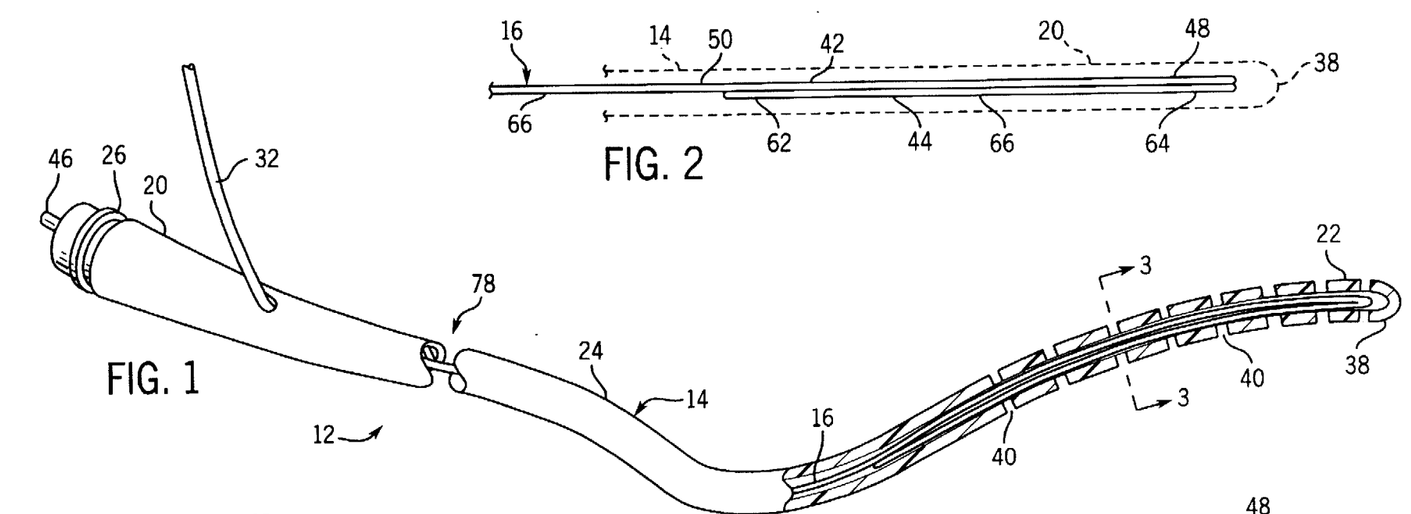
FIG. 1 is a perspective view of a stylet and tube assembly according to the invention.
FIG. 2 is a side elevational view of a portion of a stylet according to the invention with the tube shown in phantom lines.
FIG. 3 is a cross-sectional view of the stylet and tube assembly taken along lines 3—3 of FIG. 1.
Figure 3:
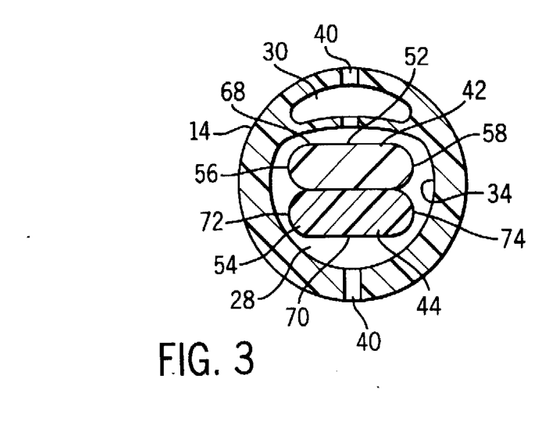

The distal end 22 of the tube 14 terminates in a rounded tip 38 which closes the end of the primary lumen 28. A plurality of apertures 40 are formed in the distal end 22 of the tube 14 provide fluid communication between the primary lumen 28, secondary lumen 30 and the exterior of the tube 14. The structure of the preferred embodiment of the tube described above is commercially available from Sherwood Medical Co. of St. Louis, Mo. and is sold under the trademark Salem Sump Tube™.

The stylet 16 comprises a first filament 42 and a second filament 44 which are joined to one another. The first filament comprises a proximal end 46, a distal end 48 and a body 50 intermediate the proximal and distal ends. Similarly, the second filament 44 comprises a proximal end 62, distal end 64 and body 66 intermediate to the proximal and distal ends. Preferably, the first and second filaments 42, 44 are substantially rectangular in cross section wherein the first filament 42 has a top surface 52, a bottom surface 54 and a pair of opposed side surfaces 56, 58, and the second filament has a top surface 68, bottom surface 70 and a pair of opposed side surfaces 72, 74. As seen in FIG. 3, the first and second filaments 42, 44 are dimensioned such that the bottom surface 54 of the first filament 42 abuts the top surface 68 of the second filament 44 and the top and side walls 52, 56, 58 of the first filament 42 and bottom and side walls 70, 72, 74 of the second filament 44 are closely adjacent to the interior surface 34 of the primary lumen 28.

The length of the stylet 16 where the second filament 44 is mounted to the first filament is known as the active portion 76 and the remainder of the stylet is the static portion 78.

The proximal and distal ends 62, 64 of the second filament 44 are joined to the first filament 42 such that the bottom surface 54 of the first filament 42 is closely adjacent to the top surface 68 of the second filament 44. Preferably, the first and second filaments are formed from a plastic - type material such as acetal or nylon. However, any flexible, durable material will be suitable.

If the filaments are formed from nylon, or some other thermoplastic material then the proximal and distal ends 62, 64 of the second filament 44 may be joined to the first filament 42 by a suitable process such as heat staking, ultrasonic welding or adhesive. Alternatively, the filaments could be extruded or injection molded and then partially slit along the length thereof to create the first and second filaments and the joined proximal and distal ends of the second filament.

Figure 4:
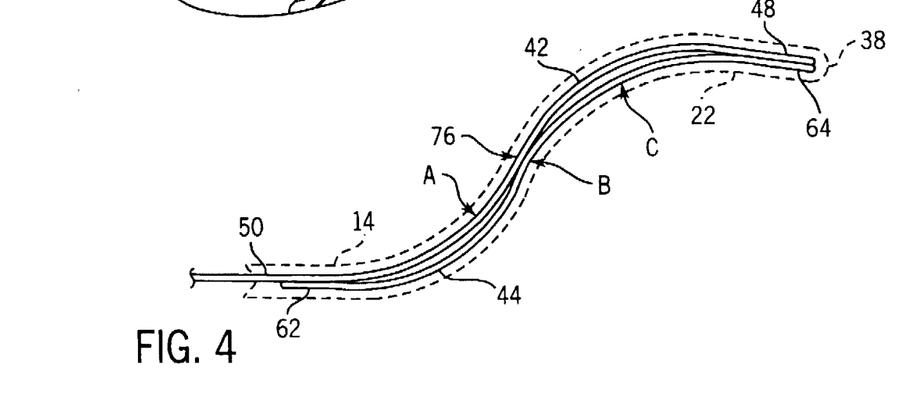
FIG. 4 is a side elevational view the stylet and tube assembly deformed in a first direction.
Figure 5:
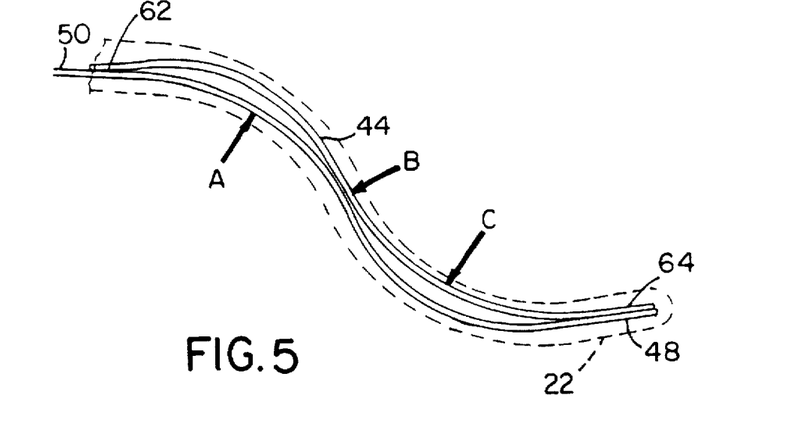
FIG. 5 is a side elevational view of the stylet and tube assembly deformed in a second direction.

As seen in FIGS. 4 and 5, the tube 14 is selectively deformable by manipulation of the active portion 76 of the stylet 16 inside the tube 14. The stylet 16 is adapted to permit controlled deformation of one portion of the stylet 16 and tube 14 in response to manipulation of a second portion of the stylet 16 and tube 14. In other words, deformation of the stylet 16 and tube 14 adjacent to the proximal end 62 of the second filament 44 will result in a corresponding, opposite deformation of the stylet 16 and tube 14 adjacent the distal end 64 of the second filament 44. This cause and effect action is the result of the joined structure of the first and second filaments 42, 44. As noted above, the bottom surface 54 of the first filament 42 preferably abuts the top surface 68 of the second filament 44 when the stylet 16 is in a relaxed position and the proximate and distal ends 62, 64 of the second filament 44 are joined to the first filament 42. Therefore, bending of the second filament 44 when the first and second filaments are received inside the tube 14 results in corresponding bending of the first filament 42. If opposed forces are applied to the tube 14 and stylet 16 in a direction substantially normal to the abutting bottom and top surfaces 54, 68 of the first and second filaments 42, 44 respectively, then these forces will cause a corresponding deformation of the stylet 16 and tube 14 about a first radius having a prescribed centerpoint. The forces are identified by force vectors A and B in FIGS. 4 and 5. As the first filament 42 is bent about a radius centered at the force vector A, then the second filament 44 must similarly deflect because the ends of the second filament are joined to the first filament. However, the thickness of the two abutting filaments prevents the second filament 44 from rotating about the same radius and centerpoint as the deflection of the first filament 42. In fact, the second filament rotates about a second radius having a second centerpoint. Deflection of the first and second filaments, which are joined together, about two different radii of curvature will necessarily result in a second deformation of the first and second filaments about two different radii of curvature. The second deformation is opposite to the first deformation and compensates for the differing radii of curvature of the joined first and second filaments 42, 44.

As seen in FIG. 4, the stylet is deflected by the application of forces in the direction of force vectors A and B. The deflection of the first filament 42 about a first radius of curvature at force vector A results in a second radius of curvature of the second filament 44 at the force vector A. The corresponding, opposed deflection of the first and second filaments 42, 44 occurs at arrow C.

The second filament 44 has assumed a radius of curvature at arrow C which is substantially identical to the first radius of curvature of the first filament 42 at force vector A. Similarly, the first filament 42 has assumed a radius of curvature at arrow C which is substantially identical in vector, but opposed in direction to the second radius of curvature of the second filament 44 at force vector A. The difference in the radii of curvature between the first and second filaments at the arrows A and C is based primarily on the thickness of the filaments. Varying the thickness of one or both of the filaments will result in a corresponding alteration of the radii of curvature as the filaments are deformed with respect to one another along a plane which is substantially perpendicular to the abutting surfaces of the two filaments.

FIG. 4 shows deflection of the first and second filaments in a first direction along a plane substantially perpendicular to the abutting surfaces of the first and second filaments. FIG. 5 shows a similar deflection of the first and second filaments in a second direction along the plane substantially perpendicular to the abutting surfaces of the first and second filaments.

The structure of the filaments 42, 44 according to the invention permits controlled deflection of the distal portion of the tube and stylet through manipulation of a portion of the tube 14 proximal of the point of desired deflection. The location of the second, opposed deflection along the length of the active portion of the stylet 16 can also be controlled. Generally, the centerpoint of the second, opposed deflection will be spaced from the joined, distal ends of the first and second filaments 42, 44 a distance which is equal to the spacing of the first deflection from the joined proximal ends of the first and second filaments 42, 44. Therefore, if the user wants to create deflection of the stylet immediately adjacent to the distal tip, then the user will create the deflection of the stylet 16 immediately adjacent to the proximal ends. Similarly, if the user wants to create a broader arc across the distal portion of the stylet 16, then the user will manipulate the proximal portion of the stylet 16 a greater spaced distance from the joined proximal ends.

In the preferred embodiment, the deflection of the distal end of the stylet 16 is manipulated through the deflection of the proximal end of the second filament 44 and first filament 42. This particular orientation is the preferred embodiment of the stylet. However, it is within the scope of the invention to manipulate the distal portions of the stylets to impose deflection of a portion of the stylet proximally thereof.

Figure 6:
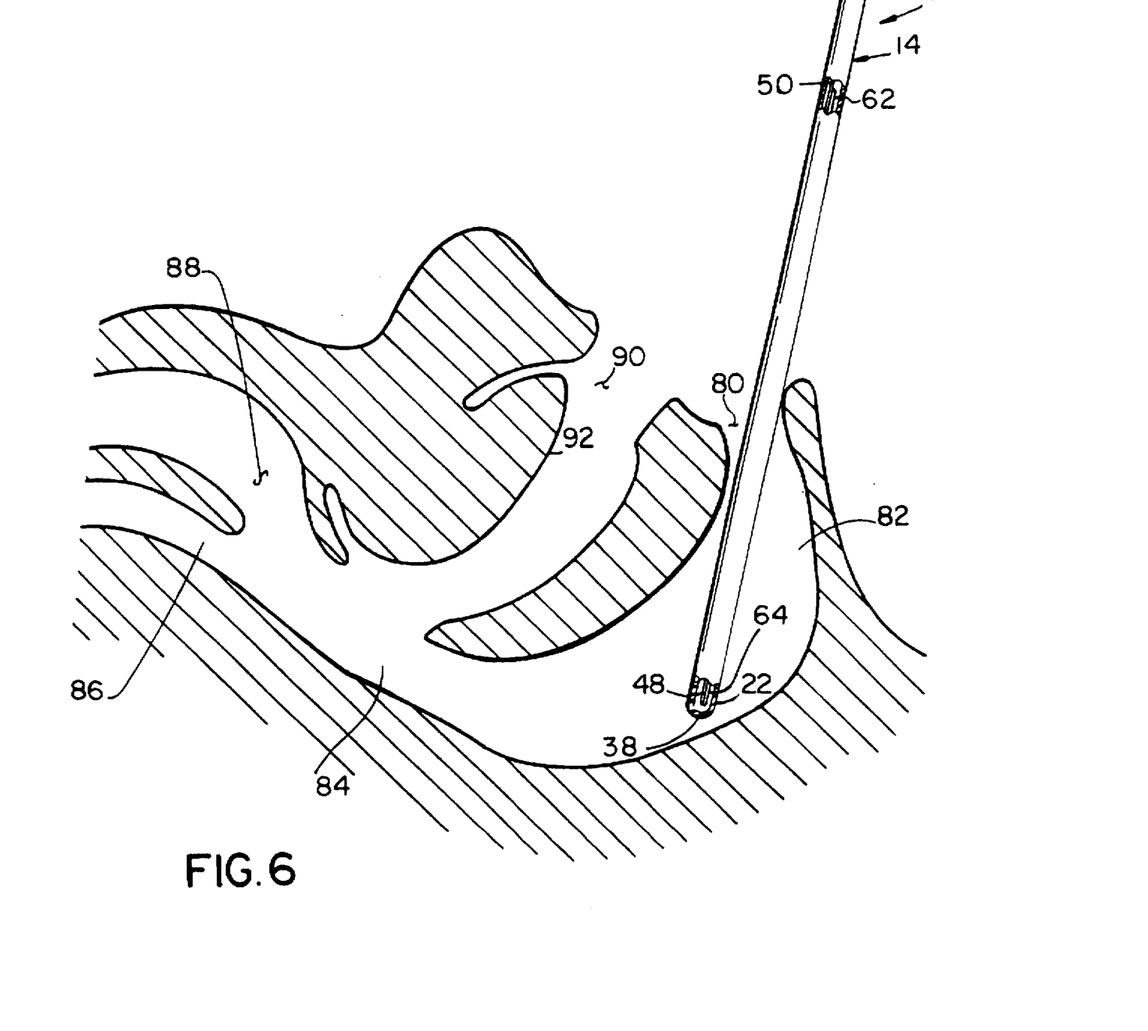
FIG. 6 is a partial sectional view of the initial stages of inserting a gastric tube nasally.
Figure 7:
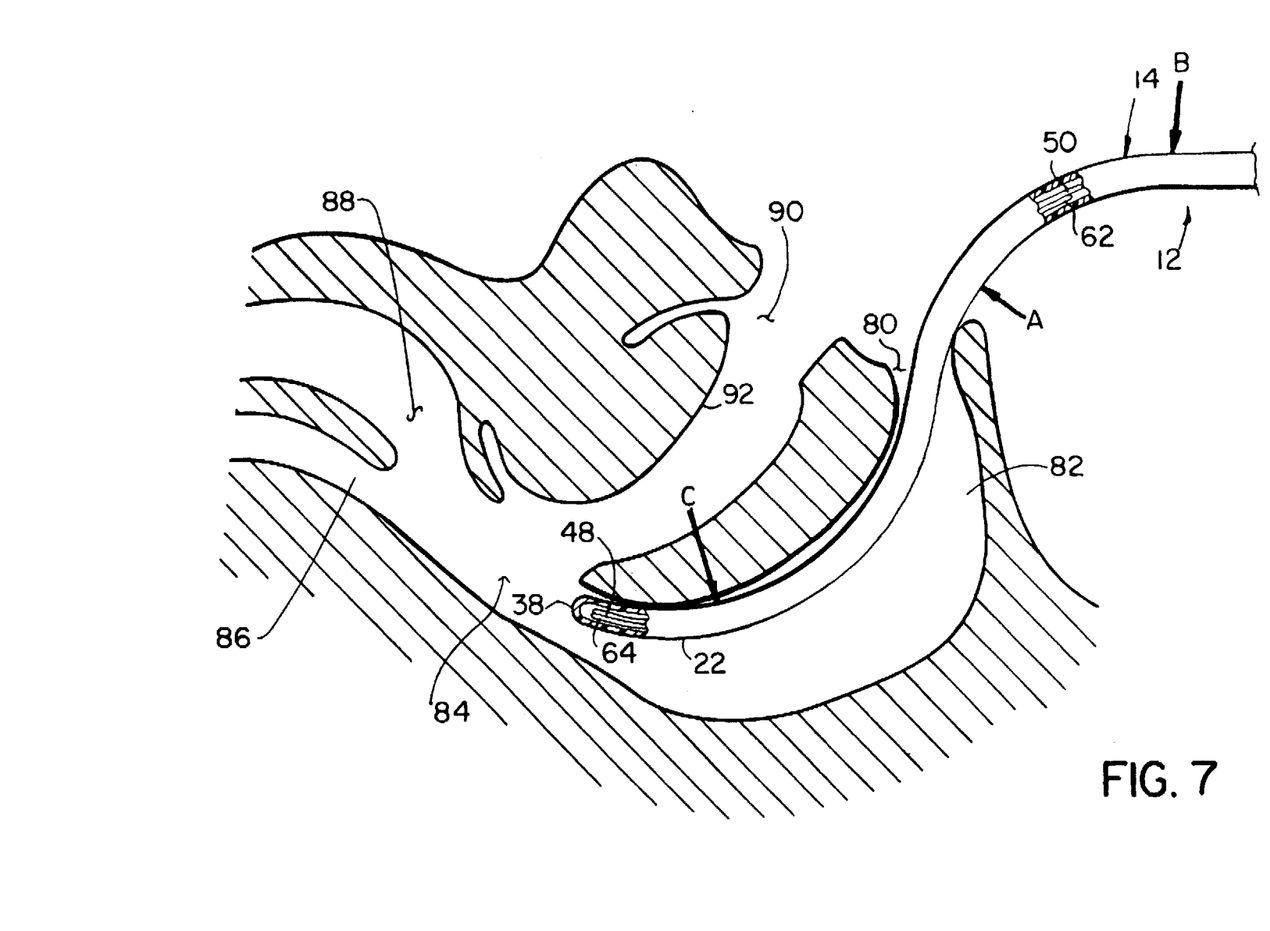
FIG. 7 is a partial sectional view of an interim step of the nasal insertion of a gastric tube utilizing a stylet according to the invention.
Figure 8:
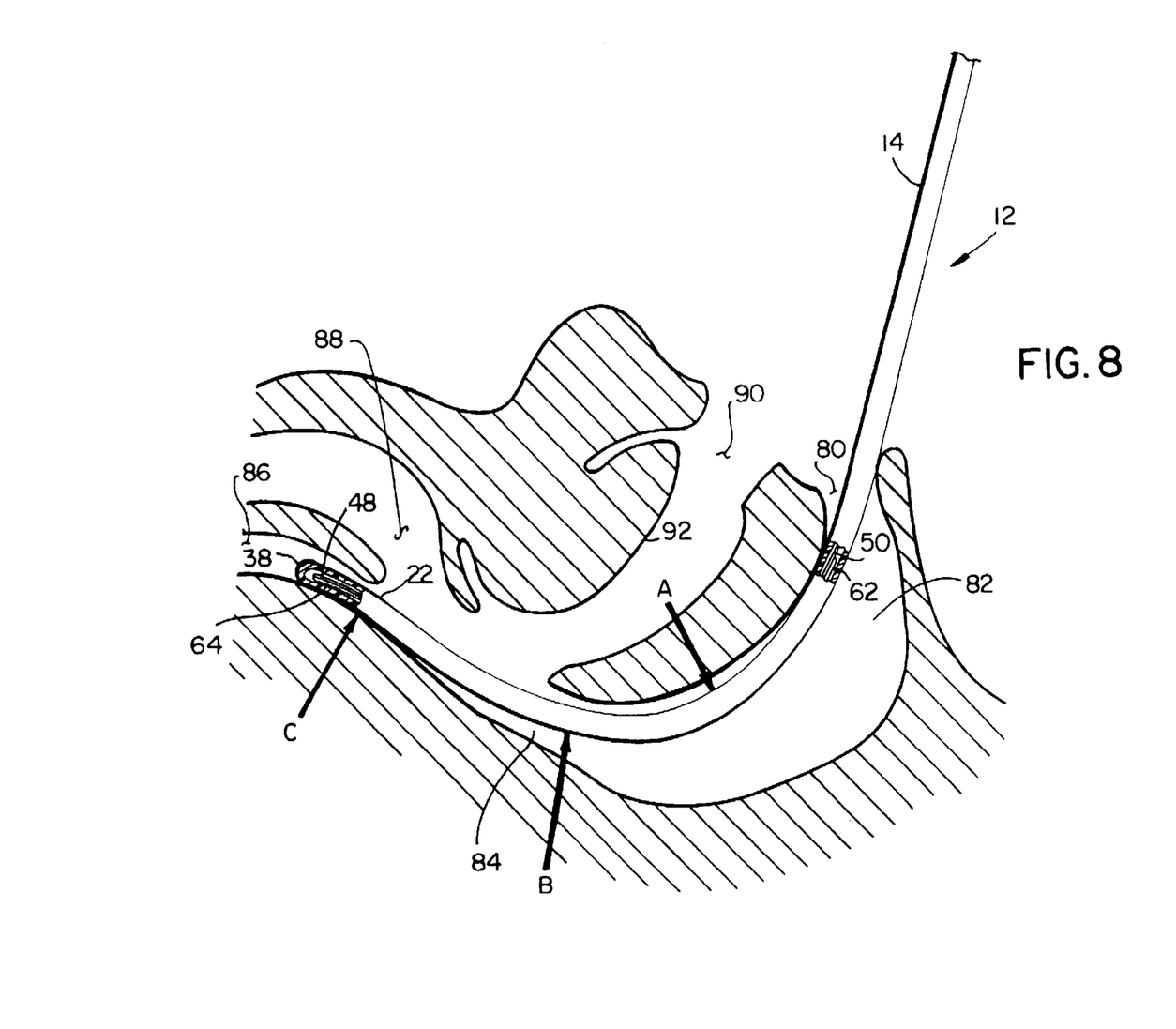
FIG. 8 is a partial sectional view of the latter stages of the nasal insertion of a gastric tube utilizing a stylet according to the invention.
Figure 10:
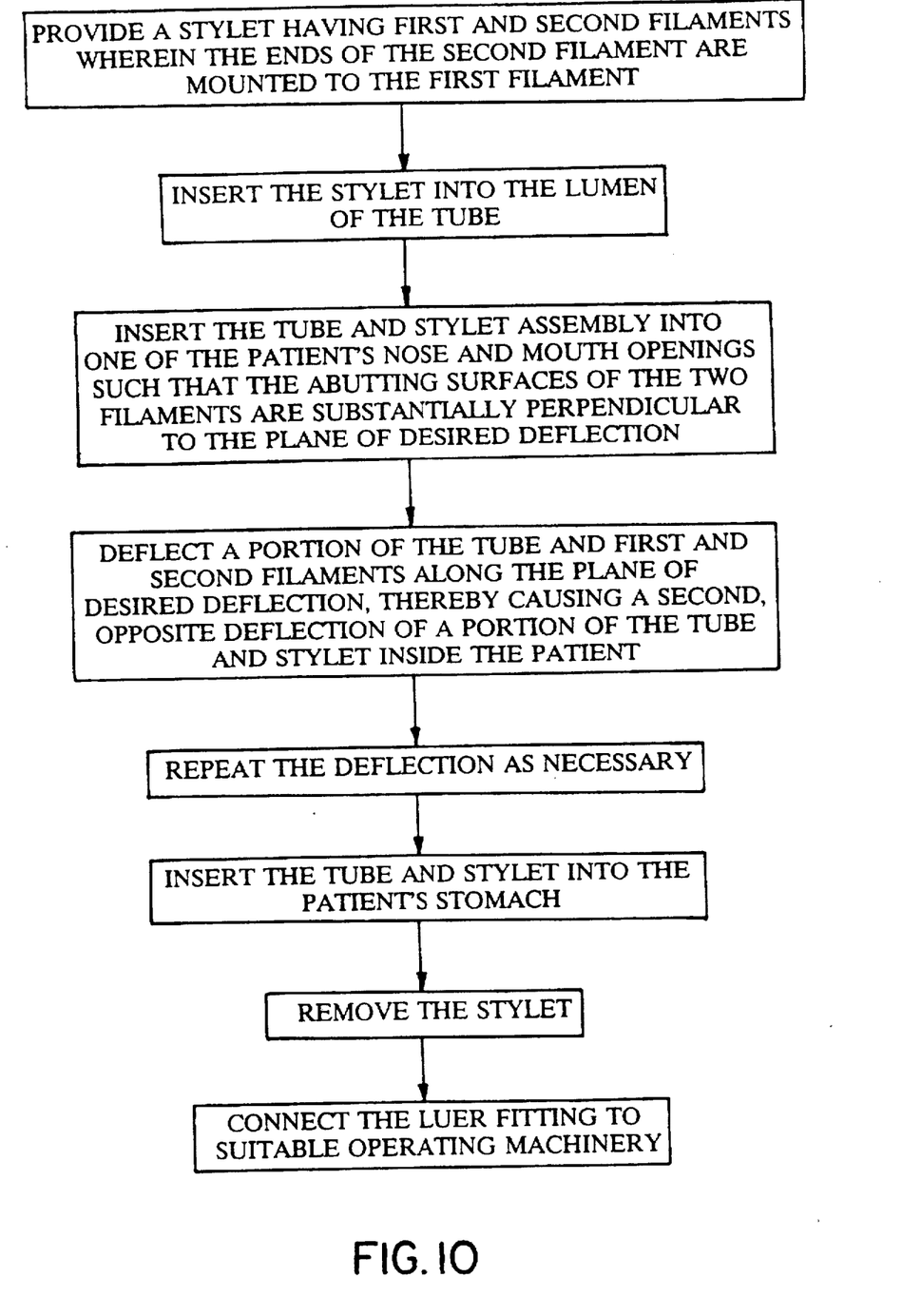
FIG. 10 is a flow chart of one embodiment of a method for nasally inserting a gastric tube utilizing a stylet according to the invention.

The ability to control deformation of the distal end of the tube and stylet assembly through manipulation of a portion of the tube and stylet spaced proximately from the distal end provides several significant advantages when inserting tubes into a contoured orifice. For example, one significant application of the stylet according to the invention is manipulating a gastric tube as it is being inserted either nasally or orally. FIGS. 6–8 show several steps of inserting a gastric tube nasally. FIG. 10 is a flow chart of the method of nasally or orally inserting the tube and stylet assembly 12 according to the invention.

As is evident from the sectional views of the patient's anatomy, the tube and stylet assembly 12 must be deflected and manipulated significantly along a plane extending substantially parallel to the longitudinal axis of the patient's neck. Therefore, the stylet 16 is mounted in the tube 14 such that plane of the adjoining first and second filaments 42, 44 is substantially perpendicular to the direction of deformation required of the tube and stylet assembly 12. As seen in FIG. 6, the nasal insertion process begins by inserting the rounded tip 38 of the tube 14 into the patient's nasal opening 80. Initially, the tube 14 and stylet 16 are initially inserted in a substantially straight configuration. The distal end 22 of the tube 14 is inserted into the nasal cavity 82 in a substantially linear configuration until the rounded tip 38 approaches the rear of the nasal cavity 82. Once this interim step is reached, the portion of the tube and stylet assembly 14 remaining outside of the patient is manipulated to cause a deformation of the distal ends of the filaments and tube 14 corresponding to the patient's anatomy.

As seen in FIG. 7, the outboard portion of the tube and stylet assembly 12 is deflected about the axis of rotation identified by force vector A in response to a force being applied in the direction of force vector B. This deflection of the first filament and proximal portion of the second filament 44 necessarily results in a corresponding, opposed deflection of the distal portions of the tube 14 and the stylet 16 received therein. The proximal portion of the stylet 16 adjacent the nasal opening 80 is deflected about the axis of curvature A. This causes the rounded tip 38 of the tube 14 to deflect upwardly as seen in FIG. 7 into the pharynx 82. The deformation of the distal end 22 of the tube 14 as seen in FIG. 7 is most easily accomplished by the user placing her thumb at the point identified by force vector A and then pivoting the proximal portion of the tube and stylet assembly 12 about her thumb, thereby resulting in deflection of the distal end 22 of the tube.

With the rounded tip 38 of the tube 14 deflected toward the pharynx 84, the tube 14 can be inserted further into the patient's nasal opening 80 until the rounded tip 38 approaches the esophagus 86 and trachea 88.

As seen in FIG. 8, the contour of the nasal passageway will, out of necessity, deflect the rounded tip 38 of the tube 14 downwardly such that the tube 14, upon further insertion, is received in the esophagus 86, as desired, rather than the trachea 88. Due to the contour of the patient's nasal cavity 82 and pharynx 84, the proximal portion of the active portion 76 of the stylet will be deflected around a radius of curvature A. This will necessarily force the distal portion 22 of the tube downwardly, thereby contacting the rear surface of the patient's pharynx 84. In this position, the tube and stylet assembly 12 can be inserted further until the distal end 22 of the tube 14 is received in the esophagus 86. Once the distal end 22 is past the pharynx 84 and the rounded tip 58 is in the esophagus 86, the stylet assembly 12 returns to the relaxed position allowing the tube 14 to enter the stomach. Once the tube 14 is properly placed into the patient's stomach, then the stylet 16 can be removed and suitable suction or feeding machinery can be attached to the luer fitting 26 of the tube 14.

In the preferred embodiment, the length of the second filament 44 is dimensioned such that the entire length of the second filament 44 is received inside the patient as the distal end 22 of the tube 14 approaches the opening of the esophagus 86. However, it is to be understood that the second filament 44 can be dimensioned to any length, depending upon the particular application. For example, it may be desired to extend the length of the second filament 44 such that a portion of the second filament 44 remains outside of the patient as the distal end 22 approaches the esophagus 86 such that the user can control deflection of the distal end 22 through hand manipulation of the first and second filaments.

Figure 9:
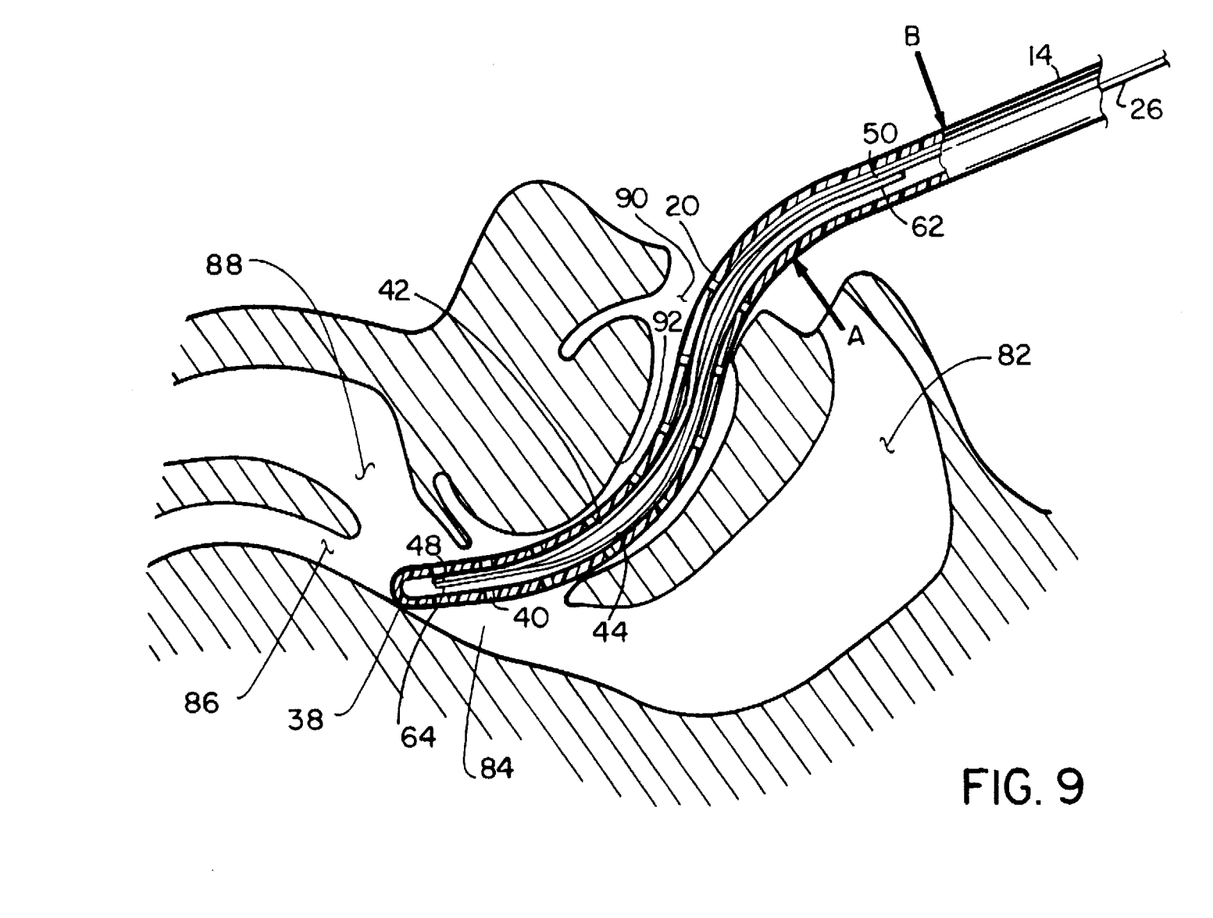
FIG. 9 is a partial sectional view of the interim stage of the oral insertion of a gastric tube utilizing a stylet according to the invention.

The preferred embodiment of the tube and stylet assembly 12 is nasally inserted into the patient's stomach. However, as seen in FIG. 9, the tube and stylet assembly may also be inserted through the patient's mouth opening 90. Similar to the nasal insertion process, the stylet 16 is received in the tube 14 such that the proximal end of the first and second filaments 42, 44 are adjacent the rounded tip 34 of the tube 14. Then, the distal end 22 of the tube 14 is inserted into the patient's mouth opening 90 and inserted rearwardly into the patient's mouth. As the rounded tip 38 approaches the rear wall of the patient's pharynx 84, the proximal portion of the second filament 44 and the first filament 42 is deflected toward the patient's forehead according to force vectors A and B to generate the desired upward, deflection of the rounded tip 38. This deflection causes the distal end 22 of the tube 14 to deflect toward the opening of the esophagus 86. Through the controlled deflection of the rounded tip, the tube 14 can be manipulated to follow the patient's anatomy without forcing the tube 14 and stylet down the patient's oral and nasal passageways thereby reducing trauma to the tissue of the patient's oral and nasal passageway.

Similar to the process described above, as the rounded tip 38 approaches the opening of the esophagus 86, the proximal portion of the second filament 44 and first filament 42 can be manipulated to guide the rounded tip 38 into the patient's esophagus 86. As described above, the tube 14 and stylet 16 can be further inserted into the patient's stomach for application of the tube. The stylet 16 can be removed from the tube once the tube is properly positioned in the esophagus 86. Alternatively, the stylet 16 can be removed after the tube 14 is properly positioned in the patient's stomach.

Through the use of the stylet 16 according to the invention, a tube 14 can be guided through a contoured passageway through simple manipulation of the tube and stylet. With this structure, a user can now control the deflection of the tube and more easily insert the tube into a patient while reducing trauma to the patient during the insertion process. All of this is accomplished with an inexpensive and easily manufactured stylet.

Figure 11:
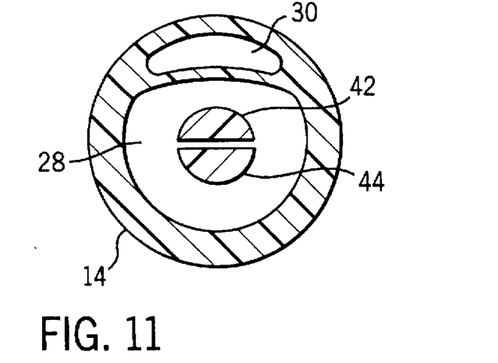
FIGS. 11–16 show different cross sectional shapes for alternative embodiments of the filaments similar to that seen in FIG. 3.
Figure 12:
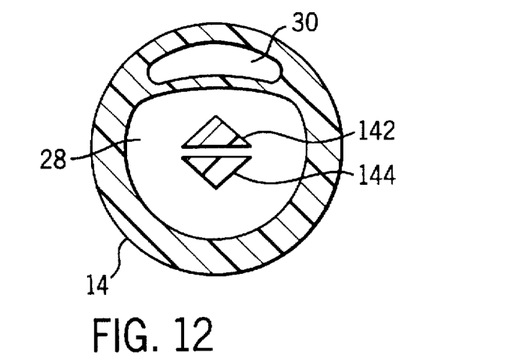
Figure 13:
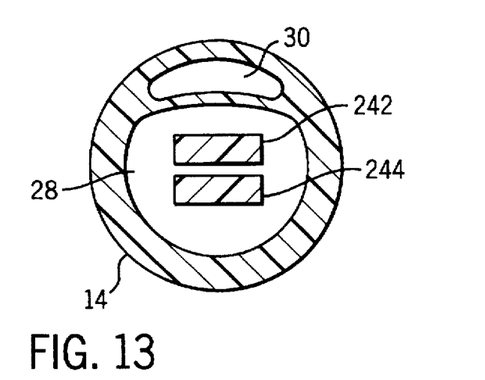
Figure 14:
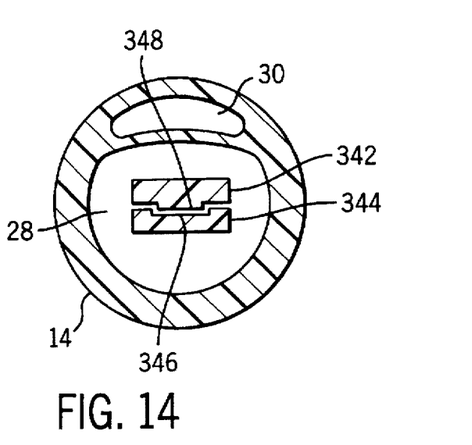
Figure 15:
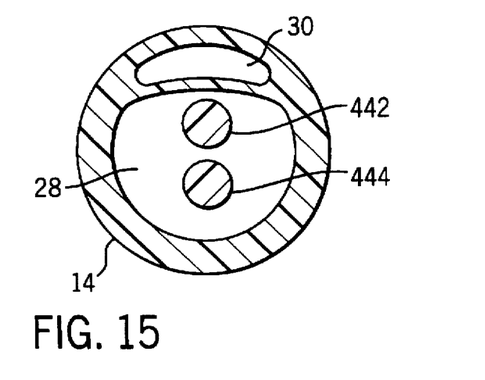
Figure 16:
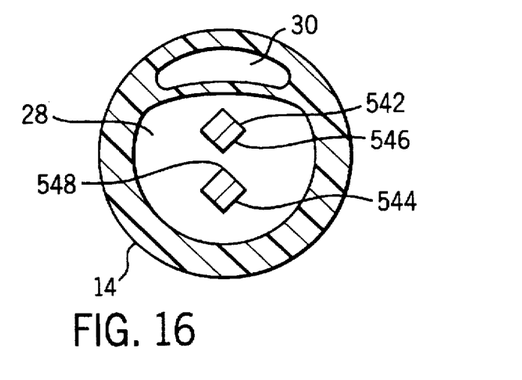

FIGS. 11–16 show alternative embodiments of the filament cross sectional shape. In FIG. 11, the preferred cross sectional shape of the filaments 42, 44 is shown namely, D-shaped. In FIG. 12, the filaments 142, 144 are triangular in cross section. FIG. 13 shows filaments 242, 244 which are rectangular in cross section and in FIG. 14, the filaments 342, 344 include a groove 346 and projection 348 on the abutting faces to ensure proper sliding movement of the filaments 342, 344 with respect to one another. In FIG. 15, the filaments 442, 444 are circular in cross section and in FIG. 16, the filaments 542, 544 are square or diamond-shaped and oriented such that the pointed corners 546, 548 of the two filaments 542, 544 abut one another.

In an alternative embodiment, one of the effective lengths of the two filaments 42, 44 could be longer than the other, thereby inducing a prebend into the stylet. With this structure, the effective length can still be manipulated to create a desired bend by deflecting the overlapping filaments.

Reasonable variation and modification are possible within the spirit of the foregoing specification and drawings without departing from the scope of the invention.

The embodiments for which an exclusive property or privilege is claimed are defined as follows:

1. A stylet and tube assembly comprising:
   a tube having a proximal end, a distal end, a body intermediate the proximal and distal ends, a prescribed length and a lumen extending therethrough; and
   a stylet received inside the lumen of the tube and comprising:
      a first filament having a proximal end, a distal end, a body portion intermediate the proximal and distal ends, a prescribed length and a longitudinal axis, the prescribed length of the first filament being greater than the prescribed length of the tube so that when the distal end of first filament is received in the tube lumen, the proximal end remains outside the tube lumen; and
      a second filament having a proximal end, a distal end, a body portion intermediate the proximal and distal ends and a longitudinal axis, the proximal and distal ends of the second filament being joined to the first filament so that the longitudinal axes of the first and second filaments define a plane;
      wherein deflection of the stylet substantially along said plane and intermediate the proximal and distal ends of the second filament results in a corresponding, opposite deflection substantially along said plane of the stylet intermediate the proximal and distal ends.

2. A stylet and tube assembly according to claim 1 wherein the first filament has a substantially flat surface extending longitudinally along a portion of the length thereof and the second filament has a substantially flat surface extending longitudinally along a portion of the length thereof and the first and second filaments are joined to one another such that the flat surfaces of the first and second filament abut one another, the flat surfaces being adapted to slide along one another as the stylet is deflected along the plane of curvature.

3. A stylet and tube assembly according to claim 2 wherein the second filament is substantially rectangular in cross section.

4. A stylet and tube assembly according to claim 3 wherein the first filament is substantially rectangular in cross section.

5. A stylet and tube assembly according to claim 1 wherein the second filament is joined to the first filament by heat staking.

6. A stylet and tube assembly according to claim 1 wherein the second filament is joined to the first filament by welding.

7. A stylet and tube assembly according to claim 1 wherein the second filament is joined to the first filament by adhesive.

8. A stylet and tube assembly according to claim 1 wherein the proximal and distal ends of the second filament are integrally molded to the first filament.

9. A stylet and tube assembly according to claim 1 wherein the distal end of the second filament is joined to the distal end of the first filament and the proximal end of the second filament is joined to the first filament at a spaced distance from the proximal end of the first filament.

10. A stylet and tube assembly comprising:
   a tube having a proximal end, a distal end, a body intermediate the proximal and distal ends and a lumen extending therethrough; and
   a stylet received inside the lumen of the tube and comprising:
      a first filament having a proximal end, a distal end, a body portion intermediate the proximal and distal ends and a longitudinal axis; and
      a second filament having a proximal end, a distal end, a body portion intermediate the proximal and distal ends and a longitudinal axis, the proximal and distal ends of the second filament being integrally molded to the first filament so that the longitudinal axes of the first and second filaments define a plane;
      wherein deflection of the stylet substantially along said plane and intermediate the proximal and distal ends of the second filament results in a corresponding, opposite deflection substantially along said plane of the stylet intermediate the proximal and distal ends.

11. A stylet according to claim 10 wherein the body of the second member is closely adjacent the first member when the second member is in a relaxed condition.

12. A stylet according to claim 10 wherein the first member has a substantially flat surface extending longitudinally along a portion of the length thereof and the second member ha s a substantially flat surface extending longitudinally along a portion of the length thereof and the first and second members are joined to one another such that the flat surfaces of the first and second members abut one another, the flat surfaces being adapted to slide along one another as the stylet is deflected intermediate the proximal and distal ends of the second member.

13. A stylet and tube assembly according to claim 12 wherein the second member is substantially rectangular in cross section.

14. A stylet and tube assembly according to claim 13 wherein the second filament is substantially rectangular in cross section.

15. A stylet adapted to selectively deform a portion of a tube, the stylet comprising:
- a first member having a proximal end, a distal end and a body intermediate the proximal and distal ends;
- a second member having a proximal end, a distal end and a body intermediate the proximal and distal ends, the proximal and distal ends of the second member being integrally molded to the first member;
- wherein a first deflection of the stylet intermediate the proximal and distal ends of the second member results in a corresponding, opposite deflection substantially along said plane of the stylet intermediate the proximal and distal ends.

16. A stylet and tube assembly according to claim 15 wherein the body of the second filament is closely adjacent the first filament when the second filament is in a relaxed condition.

17. A method of inserting a tube into an orifice comprising the steps of:
- providing a tube having a proximal end, a distal end and a lumen formed therein;
- providing a stylet comprising:
  - a first member having a proximal end, a distal end, a body intermediate the proximal and distal ends and a longitudinal axis; and
  - a second member having a proximal end, a distal end, a body intermediate the proximal and distal ends and a longitudinal axis, the proximal and distal ends of the second member being joined to the first member such that the longitudinal axes of the first and second members lie along a common plane;
- inserting the stylet into the lumen of the tube;
- inserting the distal end of the tube into an aperture of the orifice;
- deflecting the tube and stylet in a first direction intermediate the proximal and distal ends of the second member substantially along the common plane thereby causing deflection of the tube and stylet intermediate the proximal and distal ends of the second member in an opposite direction, a spaced distance from the first deflection wherein the curvature in the opposite direction corresponds to the curvature necessary to accommodate the contour of the orifice.

18. A method of inserting a tube into an orifice according to claim 17 and further comprising the step of deflecting the tube and stylet in a second direction intermediate the proximal and distal ends of the second member substantially along the common plane thereby causing deflection of the tube and stylet intermediate the proximal and distal ends of the second member in a third direction, a spaced distance from the first deflection wherein the curvature in the third direction corresponds to the curvature necessary to accommodate the contour of the orifice.

19. A method of inserting a tube into an orifice according to claim 18 and further comprising the step of removing the stylet from the tube after the tube is properly positioned.

* * * * *